(12) United States Patent
Robert et al.

(10) Patent No.: US 11,712,288 B2
(45) Date of Patent: Aug. 1, 2023

(54) BIPOLAR END EFFECTOR APPARATUS FOR A SURGICAL INSTRUMENT

(71) Applicant: Titan Medical Inc., Toronto (CA)

(72) Inventors: Rene Robert, East Greenwich, RI (US); Jonathan Hess Hills, Providence, RI (US); Timothy Norman Johnson, Freeport, ME (US)

(73) Assignee: TITAN MEDICAL INC., Toronto (CA)

(*) Notice: Subject to any disclaimer, the term of this patent is extended or adjusted under 35 U.S.C. 154(b) by 364 days.

(21) Appl. No.: 17/064,796

(22) Filed: Oct. 7, 2020

(65) Prior Publication Data

US 2021/0015545 A1    Jan. 21, 2021

Related U.S. Application Data (63) Continuation of application No. 15/744,014, filed as application No. PCT/CA2016/000193 on Jul. 11, 2016, now Pat. No. 10,849,680.

(Continued)

(51) Int. Cl.
*A61B 18/12* (2006.01)
*A61B 18/14* (2006.01)
(Continued)

(52) U.S. Cl.
CPC ....... *A61B 18/1445* (2013.01); *B25J 15/0226* (2013.01); *A61B 2017/2936* (2013.01);
(Continued)

(58) Field of Classification Search
CPC .................. A61B 18/1445; A61B 2018/00595
See application file for complete search history.

(56) References Cited

U.S. PATENT DOCUMENTS 5,395,369 A   3/1995   McBrayer et al.
5,573,534 A   11/1996  Stone
(Continued)

FOREIGN PATENT DOCUMENTS

WO    2014201538 A1    12/2014
WO    2016090459 A1    6/2016

OTHER PUBLICATIONS

International Search Report in PCT Application No. PCT/CA2016/000193 dated Sep. 21, 2016.
(Continued)

*Primary Examiner* — Daniel W Fowler
(74) *Attorney, Agent, or Firm* — Carter, DeLuca & Farrell, LLP (57) ABSTRACT

An end effector apparatus for a surgical instrument is disclosed including a housing having a first jaw mounted on a revolute joint and providing a first electrical conduction path between the housing and the first jaw. A second jaw is mounted on a revolute joint within the housing and is insulated from the housing, the jaws each having a manipulating portion and a lever arm. A yoke is received within the housing and mechanically coupled to the lever arms and to a control link and is moveable in response to movements of the control link to cause opening and closing of the jaws, the yoke being electrically insulated from the housing and the first jaw. A second electrical conduction path is provided between the control link and the second jaw. The electrical conduction paths facilitate conduction of an electrocauterization current through tissue grasped between the jaws.

15 Claims, 7 Drawing Sheets

Related U.S. Application Data

(60) Provisional application No. 62/191,886, filed on Jul. 13, 2015.

(51) Int. Cl.
  *B25J 15/02* (2006.01)
  *A61B 34/30* (2016.01)
  *A61B 17/29* (2006.01)
  *A61B 18/00* (2006.01)

(52) U.S. Cl.
  CPC ............... *A61B 2017/2945* (2013.01); *A61B 2018/00595* (2013.01); *A61B 2034/305* (2016.02)

(56) References Cited

U.S. PATENT DOCUMENTS

| | | |
|---|---|---|
| 6,228,083 B1 | 5/2001 | Lands et al. |
| 6,391,029 B1 | 5/2002 | Hooven |
| 10,849,680 B2 | 12/2020 | Robert et al. |
| 2002/0128649 A1 | 9/2002 | Bacher et al. |
| 2010/0057085 A1 | 3/2010 | Holcomb et al. |
| 2010/0312240 A1 | 12/2010 | Boulnois |
| 2013/0274741 A1 | 10/2013 | Marczyk et al. |
| 2014/0005661 A1 | 1/2014 | Shelton, IV |

OTHER PUBLICATIONS

Written Opinion received in PCT Application No. PCT/CA2016/000193 dated Sep. 21, 2016.

BIPOLAR END EFFECTOR APPARATUS FOR A SURGICAL INSTRUMENT

CROSS-REFERENCE TO RELATED APPLICATIONS

This application is a Continuation Application of U.S. patent application Ser. No. 15/744,014, filed on Jan. 11, 2018, which is a U.S. National Stage Application filed under 35 U.S.C. § 371(a) of International Patent Application No. PCT/CA2016/000193, filed Jul. 11, 2016, which claims the benefit to U.S. Provisional Patent Application No. 62/191,886, filed Jul. 13, 2015, the entire disclosure of each of which is incorporated by reference herein.

BACKGROUND

1. Field

This disclosure relates generally to an apparatus used for surgical procedures and more particularly to an end effector for a robotic and/or laparoscopic surgical instrument.

2. Description of Related Art

Remotely actuated surgical instruments may be used in laparoscopic and/or robotic surgery applications where there is an area of limited access for an operator. The surgical instrument generally includes an end effector disposed at a distal end of a shaft and an actuator portion for manipulating the end effector at a proximate end of a shaft. The end effector and a portion of the surgical instrument inserted through an incision into a body cavity of a patient while the actuator portion generally remains outside the body cavity.

End effectors having opposing pivoting jaws are used for grasping and manipulating tissue during surgery and it may be desirable to couple a high frequency alternating current through the jaws for performing electrocauterization of tissue. In some cases, the electrocauterization current may be supplied by a current generator through a unipolar end effector with the return current path being provided through a ground connection in contact with the patient's body. There however remains a need for bipolar end effectors having two jaws, in which an electrocauterization current is supplied through the first jaw, flows through tissue clamped between the two jaws, and is returned through the second jaw.

SUMMARY OF THE INVENTION

In accordance with one disclosed aspect there is provided an end effector apparatus for a surgical instrument. The apparatus includes a housing, a first jaw mounted on a revolute joint within the housing so as to provide a first electrical conduction path between the housing and the first jaw. The first jaw has a manipulating portion extending forwardly and a lever arm projecting rearwardly from the revolute joint. The apparatus also includes a second jaw mounted on a revolute joint within the housing and electrically insulated from the housing, the second jaw having a manipulating portion extending forwardly from the revolute joint and a lever arm projecting rearwardly from the revolute joint. The apparatus further includes a yoke received within the housing and mechanically coupled to the respective lever arms of the first and second jaws and to a control link, the yoke being moveable with respect to the housing in response to movements of the control link when actuated by the surgical instrument, the movement of the yoke being operable to cause opening and closing movements of the first and second jaws about the respective revolute joints. The yoke is electrically insulated from the housing and the first jaw. The apparatus also includes a second electrical conduction path between the control link and the second jaw, the first and second electrical conduction paths facilitating conduction of a electrocauterization current through tissue grasped between the first and second jaws.

The first jaw may be mounted on a first revolute joint within the housing and the second jaw is mounted on a second revolute joint within the housing.

The first jaw and the second jaw may be mounted on a common revolute joint within the housing.

The housing may include an outer clevis and the common revolute joint may include a pivot pin extending between a pair of arms associated with the outer clevis.

The yoke may include an inner clevis having arms configured to receive the respective lever arms of the first and second jaws.

The second jaw may be mounted on an insulating spacer received on the pivot pin.

The apparatus may include a torque tube coupled to the housing, the torque tube being operable to cause rotation of the housing when actuated by the surgical instrument and the torque tube may be in electrical connection with the housing for carrying the electrocauterization current.

The control link may be received within a bore of the torque tube and may further include an electrically insulating sheath between the control link and the torque tube and the control link and torque tube may be operable to connect to respective poles of a bipolar electrocautery current generator.

The torque tube, insulating sheath, and control link may be configured to flex within an articulated tool positioner to permit dexterous movement of the end effector apparatus.

The housing may include an electrically conductive material and may further include an electrically conductive washer disposed on the revolute joint between the first jaw and the housing for providing the first electrical conduction path.

The housing may include an outer clevis and the yoke may include an inner clevis having arms configured to receive the respective lever arms of the first and second jaws.

The yoke may include an electrically insulating material and the control link extends through the yoke and may have a portion in sliding contact with the second jaw for completing the second electrical conduction path.

The portion of the control link in sliding contact with the second jaw may include a conductive tab having a surface that contacts the second jaw.

The lever arms associated with the first and second jaws each may include a slot and the yoke may include a pin slidingly received within the respective slots for providing the mechanical coupling between the yoke and the lever arms.

The slot may include an arcuate slot.

The pin may include an insulated portion received within the slot in the lever arm of the first jaw, and a conductive pin portion received within the slot in the lever arm of the second jaw for completing the second electrical conduction path between the control link and the second jaw.

The housing may include an insulating material and the first electrical conduction path between the housing and the first jaw may be provided by a conductor running through the housing and having a portion in sliding contact with the first jaw.

The apparatus may include a linkage extending between the lever arm associated with at least one of the first and second jaws and the yoke for providing the mechanical coupling between the yoke and the lever arm.

In accordance with another disclosed aspect there is provided a method for actuating an end effector for a surgical instrument, the end effector includes a housing, a first jaw mounted on a revolute joint so as to provide a first electrical conduction path between the housing and the first jaw, the first jaw having a manipulating portion extending forwardly from the revolute joint and a lever arm projecting rearwardly from the revolute joint, a second jaw mounted on a revolute joint and electrically insulated from the housing, a second electrical conduction path between a control link and the second jaw, the second jaw having a manipulating portion extending forwardly from the revolute joint and a lever arm projecting rearwardly from the revolute joint, a yoke received within the housing and being mechanically coupled to respective lever arms of the first and second jaws and to a control link, the yoke being electrically insulated from the housing and the first jaw. The method involves causing movement of the yoke with respect to the housing in response to movements of the control link to cause opening and closing movements of the first and second jaws about the revolute joints, and coupling an electrocauterization current through the first and second electrical conduction paths and through tissue grasped between the first and second jaws.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
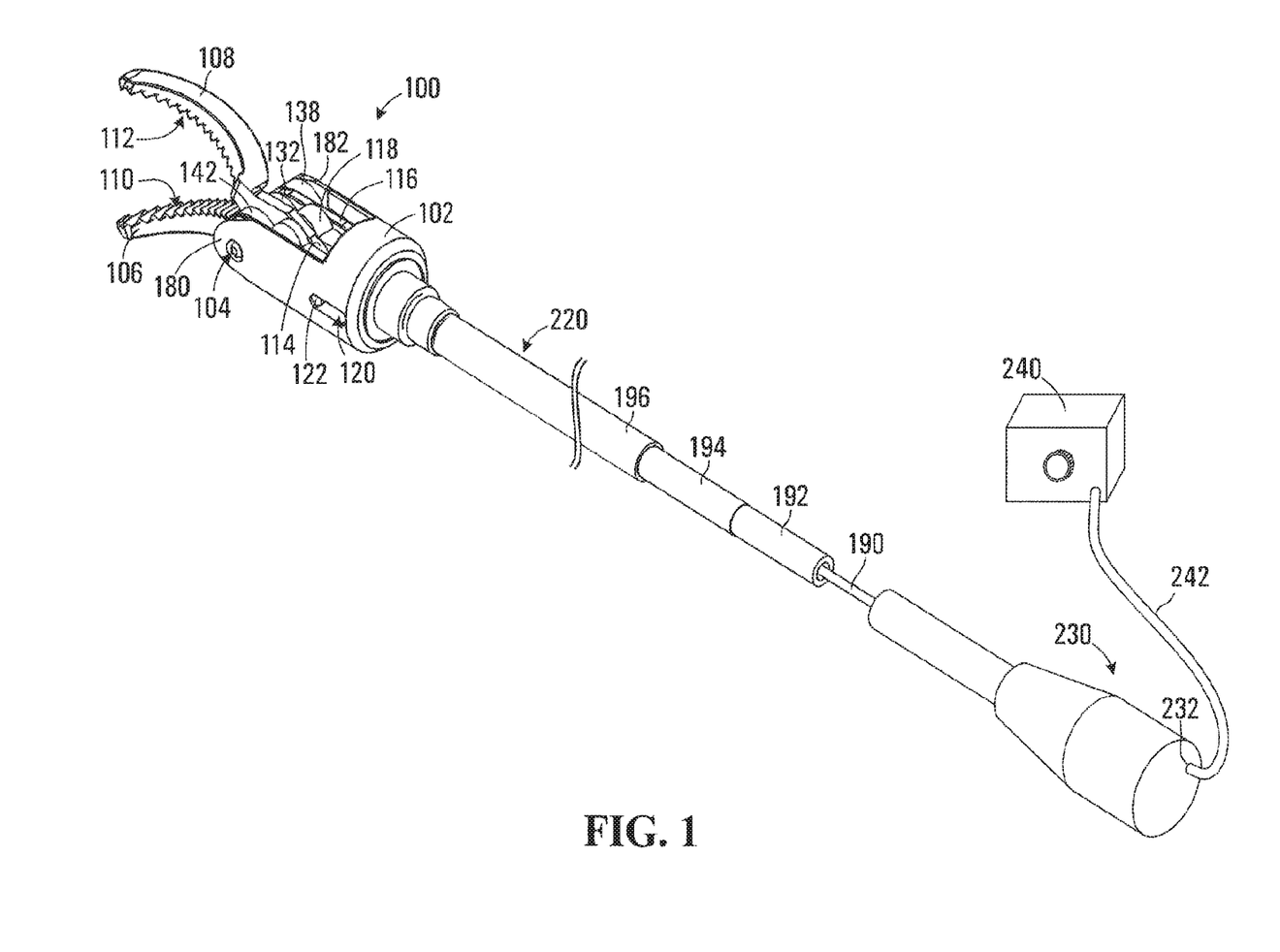
FIG. 1 is a perspective view of an end effector apparatus according to a first disclosed embodiment.

Referring to FIG. 1, an end effector apparatus according to a first disclosed embodiment is shown generally at 100. The end effector 100 is connected via a shaft 220 to a surgical instrument 230. The surgical instrument 230 includes an input 232 for receiving a current from a bipolar electrocautery generator 240 via a cable 242.

In one embodiment, the surgical instrument 230 may be an electro-mechanical interface to a robotic surgery system for controlling and actuating the end effector. For example, the surgical instrument may be configured as an articulated tool positioner as described in detail in commonly owned patent applications PCT/CA2013/001076 entitled "ARTICULATED TOOL POSITIONER AND SYSTEM EMPLOYING SAME" and PCT/CA2015/000098 entitled "ACTUATOR AND DRIVE FOR MANIPULATING A TOOL" filed on Feb. 18, 2015. In other embodiments the surgical instrument may be a hand operated laparoscopic tool actuator that is manipulated directly by a surgeon.

The end effector 100 includes a housing 102 and a revolute joint 104 received between first and second arms 180 and 182 of the housing that define an outer clevis. The end effector 100 also includes a first jaw 106 and a second jaw 108 mounted on the revolute joint 104. In this embodiment the revolute joint 104 is a common revolute joint and the first and second jaws 106 and 108 are mounted on the same revolute joint. In other embodiments, the first and second jaws 106 and 108 may be mounted on separate spaced apart revolute joints within the housing 102. The first and second jaws 106 and 108 each have respective manipulating portions 110 and 112 extending forwardly from the revolute joint 104 and respective lever arms 114 and 116 projecting rearwardly from the revolute joint. In this embodiment the first and second jaws 106 and 108 are fabricated from an electrically conductive material.

Figure 2:
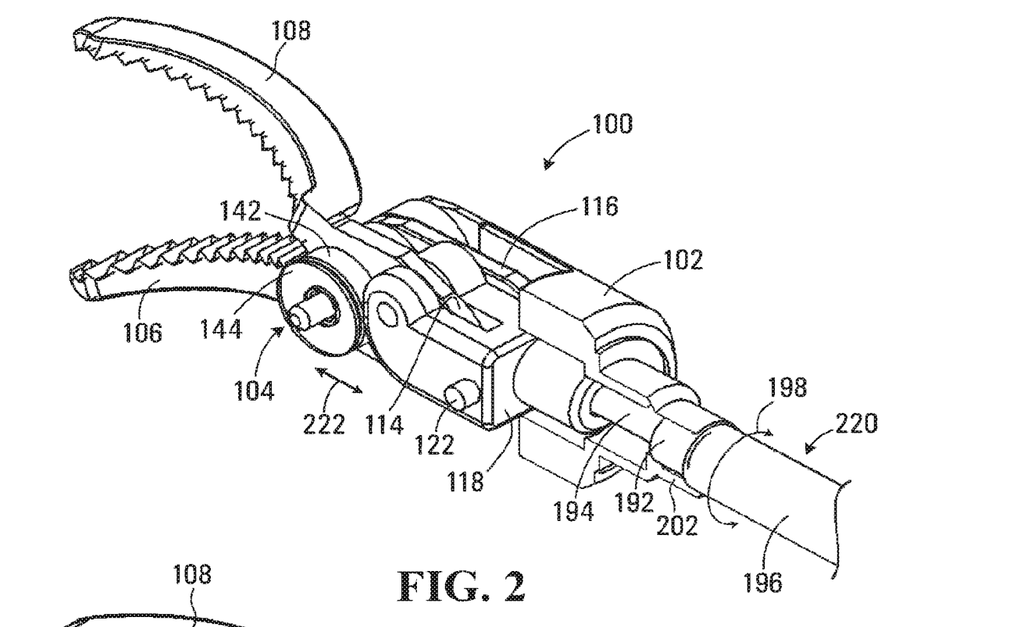
FIG. 2 is a perspective view of the end effector apparatus shown in FIG. 1 in an open condition with a housing portion partially cut away.

The end effector 100 also includes an inner clevis 118 received within the housing 102. The end effector 100 is shown in FIG. 2 in enlarged detail with the housing 102 partially removed to better show the inner clevis 118. Still referring to FIG. 1, the inner clevis 118 is reciprocally moveable within the housing 102 in a direction indicated by the arrow 222. The inner clevis 118 is sized to slide within the housing 102. In this embodiment, the housing includes a pair of slots 120 (one shown) and the inner clevis 118 includes sliding pins 122, 124, which are received in the pair of slots and guide the reciprocating motion of the inner clevis within the housing. An additional slot may be disposed on the opposite side of the housing 102 (not visible in FIG. 1 and FIG. 2) for receiving a second sliding pin associated with the inner clevis 118. The sliding pins prevent rotation of the inner clevis 118 within the housing 102, which may cause binding between surfaces of the inner clevis and surfaces of the housing.

Figure 3:
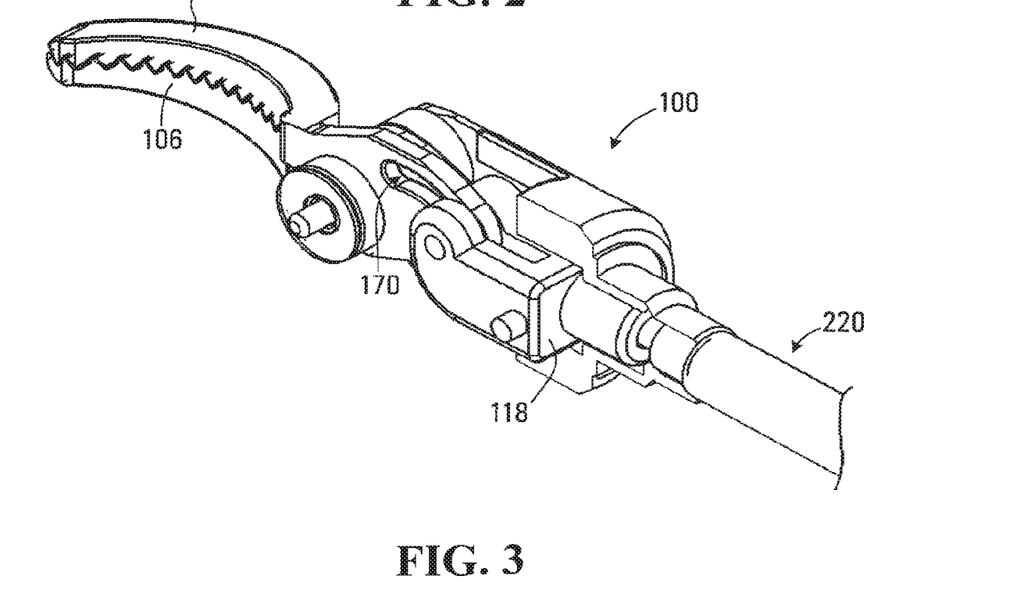
FIG. 3 is a perspective view of the end effector apparatus shown in FIG. 2 in a closed condition.

The jaws 106 and 108 are shown in an open configuration in FIG. 2, which corresponds to the inner clevis 118 having been moved forwardly toward the revolute joint 104 of the end effector 100. Referring to FIG. 3 the jaws 106 and 108 are shown in a closed configuration, which corresponds to the inner clevis 118 having been moved rearwardly away from the revolute joint 104 of the end effector 100. In this embodiment the inner clevis 118 acts as a yoke for coupling a force applied to the inner clevis to the respective lever arms 114 and 116.

In this embodiment the housing 102 is fabricated from an electrically conductive material such as stainless steel, the inner clevis 118 is fabricated from an electrically insulating material such as a plastic (for example Polyetherimide manufactured under the name Ultem by Saudi Arabia Basic Industries Corporation), and the first and second jaws 106 and 108 are fabricated from stainless steel.

Figure 4:
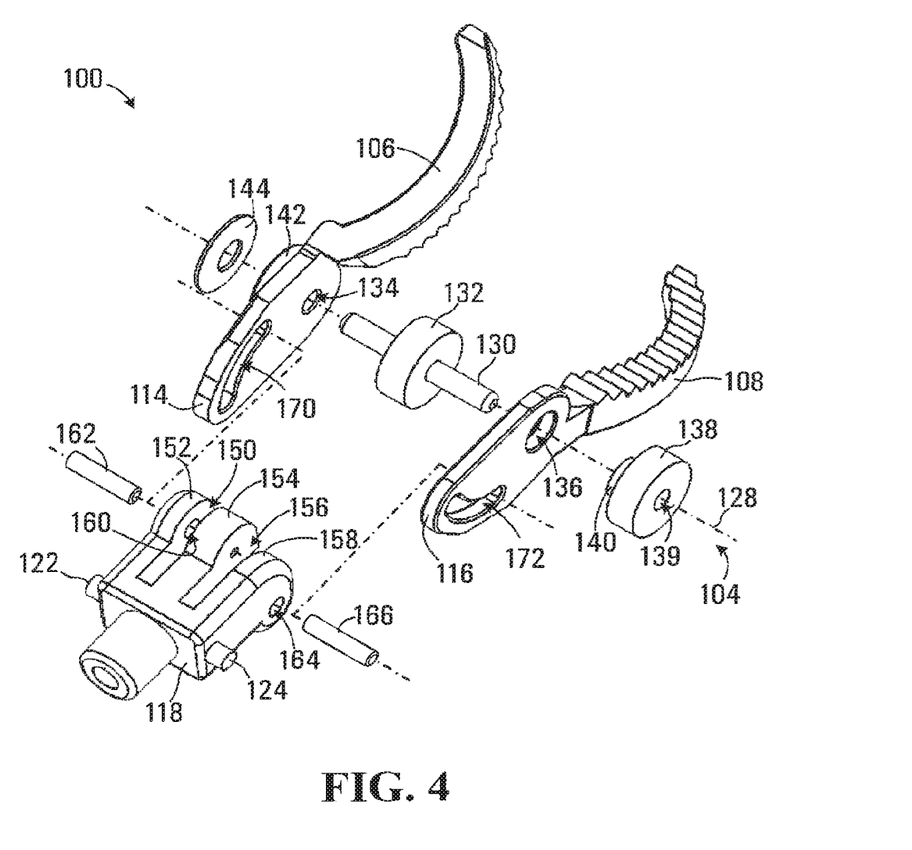
FIG. 4 is an exploded perspective view of a portion of the end effector shown in FIG. 1.

The end effector 100 is shown in exploded view in FIG. 4. Referring to FIG. 4, the revolute joint 104 is aligned along an axis 128 and includes a pivot pin 130 and an insulating spacer 132 received on the pivot pin. The pivot pin 130 is supported between the first and second arms 180 and 182 of the housing 102 (shown in FIG. 1). The insulating spacer 132 electrically insulates the first jaw 106 from the second jaw 108 when received on the pivot pin 130. The first jaw 106 includes an opening 134 and is received on the pivot pin 130 to permit the jaw to pivot freely about the pin. The revolute joint 104 also includes an insulating spacer 138, which has a protruding annular portion 140 and an opening 139 sized to be received on the pivot pin 130. The second jaw 108 further includes an opening 136 that is sized to receive the protruding portion 140 of the insulating spacer 138, which is in turn received together with the second jaw on the pivot pin 130. The insulating spacer 138 electrically insulates the second jaw 108 from the pivot pin 130.

The first jaw 106 has a protruding annular portion 142 (also shown in FIG. 2), which in this embodiment is formed as a unitary part of the electrically conductive second jaw. The revolute joint 104 further includes an electrically conductive washer 144, which is received on the pivot pin 130 and completes an electrical connection between the protruding annular portion 142 of the first jaw 106 and the housing 102. In the embodiment shown the washer 144 is a spring washer, such as a Bellville or wave washer that compresses when received between the protruding annular portion 142 and the housing 102. The spring washer 144 is compressed when the revolute joint 104 is assembled within the housing and is able to extend laterally to facilitate an electrical connection between the revolute joint 104 received between the first arm 180 of the housing 102 and the first jaw 106.

The inner clevis 118 includes a first slot 150 defined between first and second tines 152 and 154 for receiving the lever arm 114 of the first jaw 106. The inner clevis 118 also includes a second slot 156 defined between the second tine 154 and a third tine 158 for receiving the lever arm 116 of the second jaw 108. The inner clevis 118 further includes an opening 160 extending through the first tine 152 for receiving a pin 162 and an opening 164 extending through the third tine 158 for receiving a pin 166. The second tine 154 may have corresponding openings (not visible in FIG. 4) for receiving the pins 162 and 166 such that each of the pins is retained between a pair of tines.

The lever arm 114 of the first jaw 106 further includes an arcuate slot 170 and the lever arm 116 of the second jaw 108 includes an arcuate slot 172. When the end effector 100 is assembled the lever arm 114 of the first jaw 106 is received in the slot 150 and the pin 162 is pressed through the opening 160 and through the arcuate slot 170 to mechanically couple the inner clevis 118 to the first jaw. Similarly, the lever arm 116 of the second jaw 108 is received in the slot 156 and the pin 166 is pressed through the opening 164 and through the arcuate slot 172 to mechanically couple the inner clevis 118 to the second jaw. Referring back to FIG. 2, when the inner clevis 118 is actuated to move toward the revolute joint 104 the pins 162 and 166 slide forwardly along the respective arcuate slots 170 and 172 causing the respective jaws 106 and 108 to pivot about the revolute joint 104 to open.

Similarly, referring to FIG. 3, when the inner clevis 118 is actuated to move away from the revolute joint 104 the pins 162 and 166 slide rearwardly along the respective arcuate slots 170 and 172 causing the respective jaws 106 and 108 to pivot about the revolute joint 104 to close.

Referring back to FIG. 1 the shaft 220 includes a control link 190 and a torque tube 192, each of which are fabricated from electrically conducting material. The shaft 220 also includes an electrically insulating sheath 194 between the control link 190 and the torque tube 192 and an electrically insulating sheath 196 covering the torque tube. The electrically insulating sheath 194 is sized to permit free reciprocating movement of the control link 190 within the sheath. In one embodiment the torque tube 192, the insulating sheaths 194 and 196, and the control link 190 are fabricated from flexible materials that permit the shaft 220 to flex within an articulated tool positioner (not shown) that permits dexterous movement of the end effector apparatus 100.

Referring to FIG. 2, the torque tube 192 is received within a collar 202 of the housing 102.

The torque tube 192 is also mechanically coupled to the collar 202 to permit rotation of the housing 102 and thus the end effector 100 in the direction indicated by the arrow 198. The collar 202 also provides an electrical connection between the torque tube 192 and the electrically conductive housing 102. In one embodiment the torque tube 192 may be soldered, welded, or crimped to the collar 202 of the housing 102. The torque tube 192 thus provides a first electrical connection through the housing 102, through the electrically conductive washer 144 (shown in FIG. 4) and the annular portion 142 to the first jaw 106. At the same time, the insulating spacers 132 and 138 function to insulate the second jaw 108 from the first jaw 106.

Figure 5:
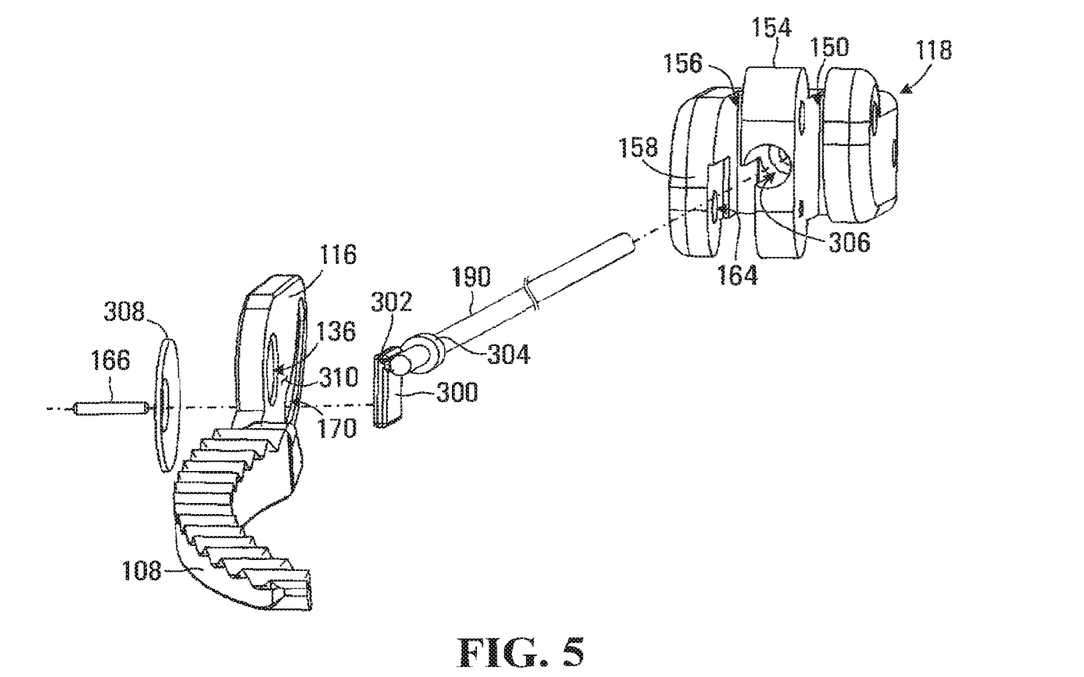
FIG. 5 is an exploded perspective view of another portion of the end effector shown in FIG. 1.
Figure 6:
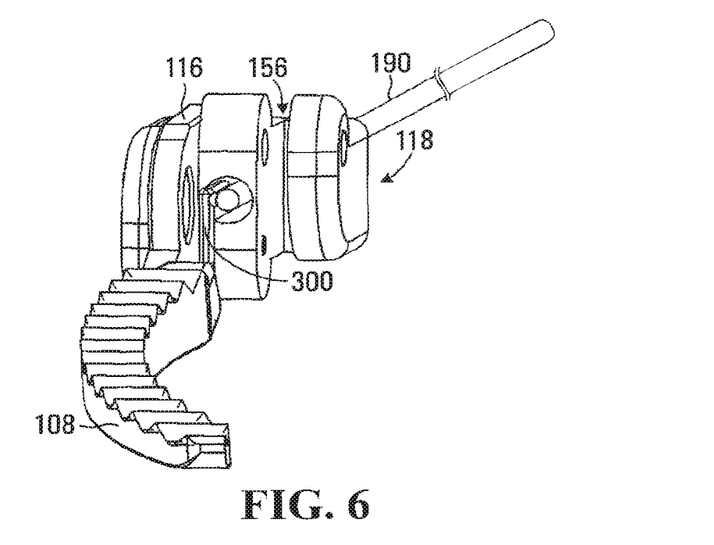
FIG. 6 is perspective view of the portion of the end effector shown in FIG. 5 in an assembled condition.

The inner clevis 118, second jaw 108, and the control link 190 of the end effector 100 are shown in exploded view in FIG. 5 and as assembled in FIG. 6. A face of the inner clevis 118 that is oriented toward the revolute joint 104 is shown while the first jaw 106 has been removed from the first slot 150 to reveal connections to the second jaw 108. As disclosed above, the inner clevis 118 is fabricated from an insulating material and there is thus no inherent electrical connection between the first jaw and the inner clevis. Referring to FIG. 5, electrical connection between the control link 190 and the lever arm 116 of the second jaw 108 is provided through a conductive tab 300. The conductive tab 300 includes a recess 302 for receiving the control link 190, which in one embodiment may be soldered to the conductive tab 300. The control link 190 also includes a ferrule 304, which is securely connected to the control link. The ferrule 304 provides an attachment point for mechanically connecting the control link 190 to the inner clevis 118 to facilitate movement of the inner clevis within the housing 102 in response to reciprocating movement of the control link. The control link 190, ferrule 304 and the conductive tab 300 are received in an opening 306 on the second tine 154 of the inner clevis 118. The ferrule 304 is mechanically secured to the inner clevis by means of an adhesive, a threaded connection, crimping or other fastening method. The inner clevis 118 is thus actuated to move with respect to the housing 102 in response to movements of the control link 190 when actuated by the surgical instrument 230 (shown in FIG. 1). The movement of the inner clevis 118 is operable to cause opening and closing movements of the first and second jaws 106 and 108 about the revolute joint 104.

The lever arm 116 of the second jaw 108 is received within the second slot 156 and a spring washer 308 is inserted between the third tine 158 and the second jaw to urge a surface 310 of the lever arm 116 into sliding electrical connection with the conductive tab 300. The second jaw 108 and spring washer 308 are retained within the second slot 156 by the pin 166, which is pressed through the opening 164 and through the arcuate slot 170 in the lever arm 116. The control link 190 thus provides a second electrical conduction path through the conductive tab 300 to the second jaw 108. The insulating spacers 132 and 138 (shown in FIG. 1) insulate the second jaw 108 from the first jaw 106 and the housing 102. The inner clevis 118 is thus electrically insulated from the housing 102 and the first jaw 106. At the same time the control link 190 is also mechanically coupled to the inner clevis 118 for actuating the inner clevis to move within the housing 102 to cause the jaws 106 and 108 to open and close.

The first and second electrical conduction paths between the control link 190 and first jaw 106 and the torque tube 192 and second jaw 108 are thus independent, and facilitate conduction of the electrocauterization current through tissue grasped between the first and second jaws 106 and 108. The two independent electrical conduction paths eliminate the need for additional cables that would usually be required to carry an electrocauterization current through the shaft and jaws. Additional cables occupy space within the shaft and may require increased shaft diameter to accommodate the cables. The disclosed embodiment, by combining the mechanical and electrical actuation functions within a single link or tube, facilitates bipolar operation of the end effector 100 without an increase in size and/or complexity of the shaft 220.

Figure 7:
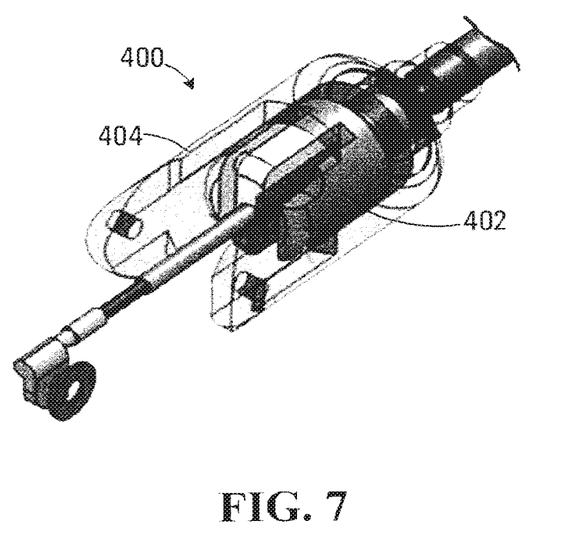
FIG. 7 is a perspective view of a portion of a housing and inner clevis of an end effector apparatus according to an alternative embodiment.

An alternative embodiment of the end effector is shown in FIG. 7 at 400. Referring to FIG. 7, an inner clevis 402 of the end effector 400 has a circular shape and is received within a housing 404 that has a circular bore for receiving the inner clevis. The inner clevis 402 is otherwise configured generally as described above in connection with the inner clevis 118, with the exception of the sliding pin 122 and the slot 120. In the end effector 400 the sliding pins may be omitted since the circular inner clevis 402 permits some rotation within the housing 404 without causing binding between the components.

Figure 8:
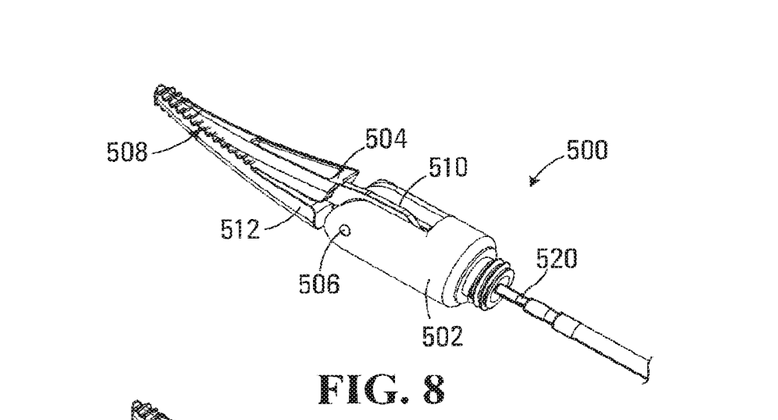
FIG. 8 is a perspective view of another disclosed embodiment of an end effector apparatus.
Figure 9:
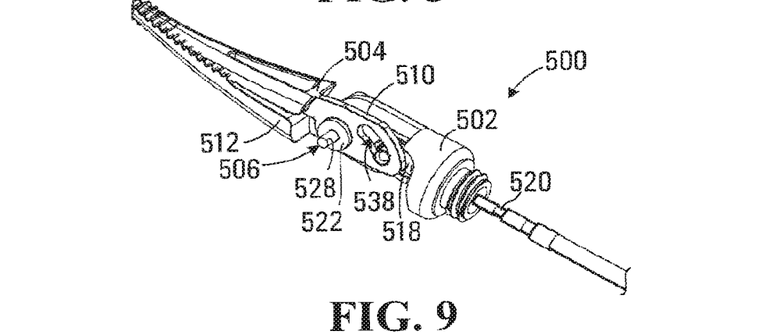
FIG. 9 is a perspective view of the end effector shown in FIG. 8 with a portion of a housing cut away.
Figure 10:
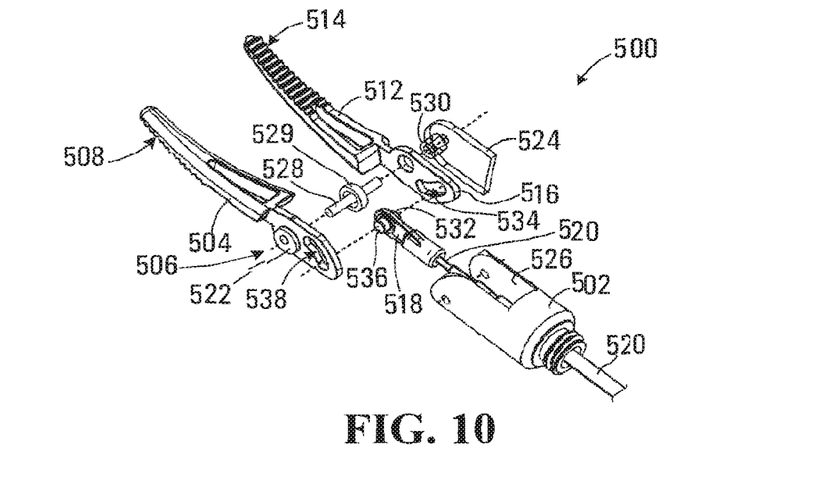
FIG. 10 is an exploded perspective view of the end effector shown in FIG. 8.

An alternative embodiment of an end effector apparatus for a surgical instrument is shown in FIGS. 8 to 10 at 500. Referring to FIG. 8, the end effector 500 includes a housing 502 and a first jaw 504 mounted on a revolute joint 506 within the housing. The first jaw 504 has a manipulating portion 508 extending forwardly and a lever arm 510 projecting rearwardly from the revolute joint (better shown in FIG. 9, where a portion of the housing 502 is cut away to reveal the lever arm 510).

The end effector 500 also includes a second jaw 512 mounted on the revolute joint 506, which in this embodiment is a common revolute joint. An exploded view of the end effector 500 is shown in FIG. 10. Referring to FIG. 10, the second jaw 512 includes a manipulating portion 514 extending forwardly from the revolute joint 506 and a lever arm 516 projecting rearwardly from the revolute joint. The lever arm 516 and manipulating portion 514 are better shown in an exploded view in FIG. 10.

Referring to FIGS. 9 and 10, the end effector 500 also includes a yoke 518 received within the housing 502 and mechanically coupled to the respective lever arms 510 and 516 of the first and second jaws 504 and 512 and to a control link 520. The yoke 518 is moveable with respect to the housing 502 in response to movements of the control link 520 when actuated by the surgical instrument. Movement of the yoke 518 causes opening and closing movements of the first and second jaws 504 and 512 about the revolute joint 506. The first and second jaws 504 and 512 are fabricated from an electrically conductive material such as stainless steel.

The revolute joint 506 includes an electrically conductive washer 522 mounted between the first jaw 504 and the housing 502, which provides a first electrical conduction path between the housing and the first jaw. In one embodiment the electrically conductive washer 522 may be a spring washer. The second jaw 512 is electrically insulated from the housing by an insulating spacer 524 that inserts in the housing between the second jaw and an arm 526 of the housing. In the embodiment shown the revolute joint 506 includes a pivot pin 528 and the insulating spacer 524 includes an insulating bushing 530 that extends through the second jaw 512 over the pivot pin. The pivot pin 528 and insulating spacer 524 thus provide a revolute mounting for the second jaw 512 within the housing 502 that insulates the second jaw from the housing. In this embodiment an additional insulating washer 529 is received on the pivot pin 528 and provides insulation between the first jaw 504 and the second jaw 512.

Referring to FIG. 10, the yoke 518 includes an electrically conductive pin 532 that is slidingly received in a slot 534 in the lever arm 516 and provides the mechanical coupling between the yoke and the lever arm. In this embodiment the pin 532 is electrically connected via the yoke 518 to the control link 520 providing a second electrical conduction path between the control link and the second jaw 512. The yoke 518 also includes a pin 536 for engaging a slot 538 in the lever arm 510 that provides the mechanical coupling between the yoke and the lever arm. However in this case the pin 536 is insulated from the yoke 518 so that the first jaw 504 remains isolated from the yoke and thus the second electrical conduction path. The yoke 518 and may be fabricated using a metal injection molding process and the electrically conductive pin 532 may be fabricated as part of the yoke. The pin 536 may be provided as an insulating insert that attaches to the yoke. In one embodiment the yoke may be a stainless steel material that is coupled directly to the control link (for example, by crimping), providing the electrical contact to the yolk. The yoke 518 is electrically insulated from the housing 502, and if necessary, an insulating overmold or other insulating components may be used to provide the electrical isolation between the yoke 518, housing 502, and the first jaw 512.

The first and second electrical conduction paths facilitate conduction of a electrocauterization current through tissue grasped between the first and second jaws 504 and 512. For example, as described above the torque tube 192 may couple to the housing to provide a connection from the bipolar electrocautery generator 240, via the housing 502, and to the first jaw 504. The control link 520 may provide a connection between the bipolar electrocautery generator 240 and the second jaw 512.

Figure 11:
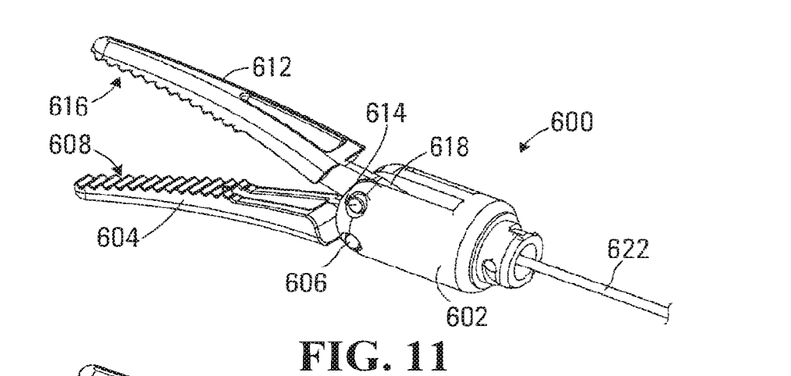
FIG. 11 is a perspective view of a further disclosed embodiment of an end effector apparatus.
Figure 12:
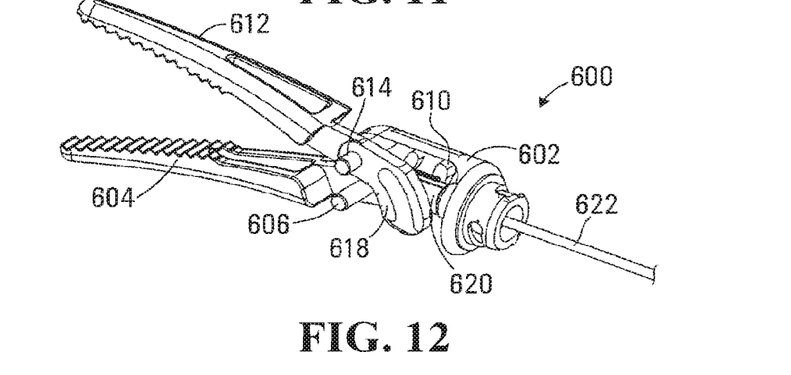
FIG. 12 is a perspective view of the end effector shown in FIG. 11 with a portion of a housing cut away.
Figure 13:
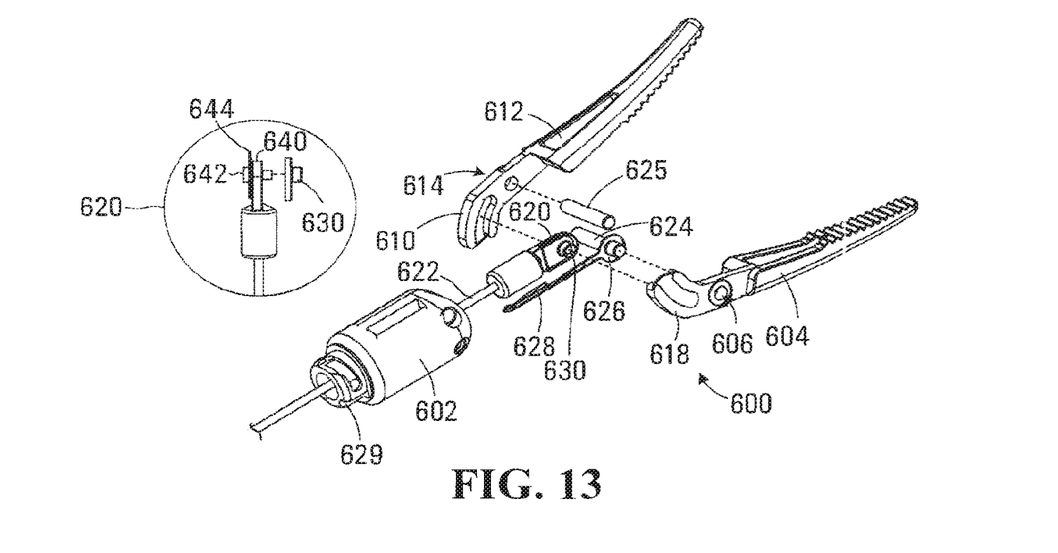
FIG. 13 is an exploded perspective view of the end effector shown in FIG. 11.

A further embodiment of an end effector apparatus for a surgical instrument is shown in FIGS. 11 to 13 at 600. Referring to FIG. 11, the end effector 600 includes a housing 602 and a first jaw 604 mounted on a first revolute joint 606 within the housing. The end effector 600 is shown in FIG. 12 with a portion of the housing 602 cut away and in exploded view in FIG. 13. The first jaw 604 has a manipulating portion 608 extending forwardly and a lever arm 610 (shown in FIGS. 12 and 13) projecting rearwardly from the revolute joint 606.

The end effector 600 also includes a second jaw 612 mounted on a second revolute joint 614. The second jaw 612 includes a manipulating portion 616 extending forwardly from the revolute joint 606 and a lever arm 618 projecting rearwardly from the revolute joint. In this embodiment the first revolute joint 606 and the second revolute joint 614 are vertically separated within the housing 602, which may improve gripping force when the first and second jaws 604 and 612 are actuated to close.

Referring to FIGS. 11 and 12, the end effector 600 also includes a yoke 620 received within the housing 602 and mechanically coupled to the respective lever arms 610 and 618 of the first and second jaws 604 and 612 and to a control link 622. The yoke 620 is moveable with respect to the housing 602 in response to movements of the control link 622 when actuated by the surgical instrument. Movement of the yoke 620 causes opening and closing movements of the first and second jaws 604 and 612 about the respective revolute joints 606 and 614. The first and second jaws 604 and 612 are fabricated from an electrically conductive material such as stainless steel.

The embodiment shown in FIGS. 11-13 differs from that shown in FIGS. 8-10 in that the housing 602 is fabricated from a non-conductive material such as a Polyetherimide and thus there is no electrical connection directly between the housing and the either of the jaws 604 and 612. Referring to FIG. 13, the first revolute joint 606 includes a pin 624 and an electrically conductive washer 626 (such as a spring washer) mounted on the pin. The washer 626 also includes a conductor portion 628 that runs through the housing and emerges at a slot 629 in the rear of the housing 602. When assembled the washer 626 contacts the first jaw 604 and thus provides a first electrical conduction path through the conductor portion 628, via the washer 626, and to the first jaw 604. The first jaw 604 thus remains insulated from the housing 602, since the housing is non-conductive.

The second revolute joint 614 includes a pin 625 for mounting the second jaw 612, which is also electrically insulated from the housing. The yoke 620 is shown in further detail in an insert in FIG. 13. The yoke 620 includes an electrically conductive center portion 640 and also includes an insulated pin 630 that slidingly engages a slot 632 in the lever arm 610. The insulated pin 630 is provided as an insulating insert. The yoke 620 also includes a conductive pin 642 and conductive spring washer, which when engaged with a slot 646 in the lever arm 618 provides a second electrical conduction path through the control link 622, via the yoke 620, to the second jaw 612. The yoke 620 need not be insulated from the housing 602 in this embodiment since the housing is non-conductive.

The first and second electrical conduction paths facilitate conduction of a electrocauterization current through tissue grasped between the first and second jaws 604 and 612. While specific embodiments have been described and illustrated, such embodiments should be considered illustrative only and not as limiting the invention as construed in accordance with the accompanying claims.

What is claimed is:

1. An end effector apparatus for a surgical instrument, the apparatus comprising:
   a housing;
   a first jaw mounted on a revolute joint within the housing so as to provide a first electrical conduction path between the housing and the first jaw, the first jaw having a manipulating portion extending forwardly and a lever arm projecting rearwardly from the revolute joint, the revolute joint defining a revolute axis;
   a second jaw mounted on the revolute joint within the housing and electrically insulated from the housing, the second jaw having a manipulating portion extending forwardly from the revolute joint and a lever arm projecting rearwardly from the revolute joint;
   an inner clevis received within the housing and mechanically coupled to the respective lever arms of the first and second jaws and to a control link, the inner clevis being moveable with respect to the housing in response to movements of the control link along a control axis extending orthogonal to the revolute axis when actuated by the surgical instrument, the movement of the inner clevis being operable to cause opening and closing movements of the first and second jaws about the respective revolute joints, the inner clevis being electrically insulated from the housing and the first jaw, the inner clevis including:
      a first tine defining a first tine opening extending parallel to the revolute axis and being spaced a radial distance from the control axis;
      a second tine disposed adjacent to and spaced apart from the first tine to define a first slot therebetween, wherein the lever arm of the first jaw is disposed within the first slot, the second tine defining:
         a first opening axially aligned with the opening of the first tine, and spaced a radial distance from the control axis; and
         a second opening, parallel to the first opening, and spaced a radial distance from the control axis, on a side opposite the first opening; and
      a third tine disposed adjacent to and spaced apart from the second tine to define a second slot therebetween, the third tine defining a third tine opening extending parallel to the revolute axis and being axially aligned with the second opening of the second tine; and
   a second electrical conduction path between the control link and the second jaw, the first and second electrical conduction paths facilitating conduction of an electrocauterization current through tissue grasped between the first and second jaws.

2. The apparatus of claim 1, further comprising a first pin disposed within the first tine opening and the first opening of the second tine, wherein the first pin extends through an arcuate slot formed in the lever arm of the first jaw.

3. The apparatus of claim 2, further comprising a second pin disposed within the third tine opening and the second opening of the second tine, wherein the second pin extends through an arcuate slot formed in the lever arm of the second jaw.

4. The apparatus of claim 3, wherein the inner clevis defines a central opening extending longitudinally therethrough and disposed at least partially within the second tine.

5. The apparatus of claim 1, wherein the first jaw and the second jaw are each mounted on the revolute joint within the housing.

6. The apparatus of claim 1, wherein the housing includes an outer clevis and wherein the revolute joint includes a pivot pin extending between a pair of arms associated with the outer clevis.

7. The apparatus of claim 6, wherein the second jaw is mounted on an insulating spacer received on the revolute joint.

8. The apparatus of claim 1, further comprising a torque tube coupled to the housing, the torque tube being operable to cause rotation of the housing when actuated by the surgical instrument and wherein the torque tube is in electrical connection with the housing for carrying the electrocauterization current.

9. The apparatus of claim 8, wherein the control link is received within a bore of the torque tube and further comprising an electrically insulating sheath between the control link and the torque tube and wherein the control link and torque tube are operable to connect to respective poles of a bipolar electrocautery current generator.

10. The apparatus of claim 9, wherein the torque tube, insulating sheath, and control link are configured to flex within an articulated tool positioner to permit dexterous movement of the end effector apparatus.

11. The apparatus of claim 1, wherein the housing comprises an electrically conductive material and further comprising an electrically conductive washer disposed on the revolute joint between the first jaw and the housing for providing the first electrical conduction path.

12. The apparatus of claim 1, wherein the inner clevis includes an electrically insulating material and wherein the control link extends through the inner clevis and has a portion in sliding contact with the second jaw for completing the second electrical conduction path.

13. The apparatus of claim 12, wherein the portion of the control link in sliding contact with the second jaw includes a conductive tab having a surface that contacts the second jaw.

14. The apparatus of claim 1, wherein the housing includes an insulating material and wherein the first electrical conduction path between the housing and the first jaw is provided by a conductor running through the housing and having a portion in sliding contact with the first jaw.

15. The apparatus of claim 1, further comprising a linkage extending between the lever arm associated with at least one of the first and second jaws and the inner clevis for providing the mechanical coupling between the inner clevis and the lever arm.

* * * * *